United States Patent [19]

Felix

[11] 4,351,665

[45] Sep. 28, 1982

[54] SULFINOATE HERBICIDAL ANTIDOTES

[75] Inventor: Raymond A. Felix, Richmond, Calif.

[73] Assignee: Stauffer Chemical Company, Westport, Conn.

[21] Appl. No.: 241,901

[22] Filed: Mar. 9, 1981

Related U.S. Application Data

[60] Division of Ser. No. 140,079, Apr. 14, 1980, abandoned, which is a continuation-in-part of Ser. No. 52,389, Jun. 27, 1979, abandoned.

[51] Int. Cl.$^3$ ...................... A01N 41/00; A01N 33/02

[52] U.S. Cl. .......................................... 71/103; 71/88; 71/100; 71/121

[58] Field of Search ................................. 71/121, 103

[56] References Cited

U.S. PATENT DOCUMENTS

| | | | |
|---|---|---|---|
| 2,885,435 | 5/1959 | Pursglove | 71/103 |
| 2,927,126 | 3/1960 | Pursglove | 71/103 |
| 3,124,447 | 3/1964 | Wineman et al. | 71/103 |
| 3,131,509 | 5/1964 | Hoffmann | 71/103 |
| 3,257,190 | 6/1966 | Soper | 71/121 |
| 3,930,836 | 1/1976 | Arneklev | 71/103 |
| 4,073,638 | 2/1978 | MacMurray | 71/121 |
| 4,087,271 | 5/1978 | Rheinecker | 71/98 |
| 4,137,066 | 1/1979 | Gaughan | 71/118 |

OTHER PUBLICATIONS

Silhanek et al., "Some Reactions, etc." (1976), CA 86 No. 139337j, (1977).

*Primary Examiner*—Glennon H. Hollrah

*Attorney, Agent, or Firm*—Harry A. Pacini

[57] ABSTRACT

Sulfinoate compounds have the formula $$RO\overset{\overset{O}{\|}}{S}R_1$$

in which R and $R_1$ are each haloalkyl having 1–4 carbon atoms. The compounds have utility as herbicidal antidotes for the protection of crops from thiocarbamate or trifluralin herbicidal injury.

5 Claims, No Drawings

SULFINOATE HERBICIDAL ANTIDOTES

This is a division of application Ser. No. 140,079, filed Apr. 14, 1980, now abandoned which application is a continuation-in-part application of copending application Ser. No. 52,389, filed June 27, 1979, now abandoned.

BACKGROUND OF THE INVENTION

Uses of Herbicides

A herbicide is a compound which controls or modifies plant growth, e.g., killing, retarding, defoliating, desiccating, regulating, stunting, tillering, stimulating, and dwarfing. "Plant" refers to all physical parts, including seeds, seedlings, saplings, roots, tubers, stems, stalks, foliage, and fruits. "Plant growth" is meant to include all phases of development from seed germination to natural or induced cessation of life.

Herbicides are generally used to control or eradicate weed pests. They have gained a high degree of commercial success because it has been shown that such control can increase crop yield and reduce harvesting costs.

Herbicidal effectiveness is dependent upon several variables. One of these is the time or growth related method of application. The most popular methods of application include: pre-plant incorporation into the soil; pre-emergence surface treatment of seeded soil; and post-emergence treatment of the plant and soil.

The most important determinant of herbicidal effectiveness is the susceptibility of the beneficial crop and selectivity toward weeds. Certain herbicidal compounds are phytotoxic to some weed species but not to others.

A manufacturer of a herbicide generally recommends a range of rates and concentrations calculated to maximize weed control. The range of rates varies from approximately 0.1 to 50 pounds per acre (lb/A) (0.112 to 56 kilograms per hectare (k/ha)), usually from 0.1 to 25 lb/A (0.112 to 28 k/ha). The actual amount used depends upon several considerations including particular weed susceptibility and overall cost limitations.

Some herbicides display exclusive selectivity toward weed species. Many are toxic to both weeds and the intended crop beneficiary. Therefore, a particular herbicide's use may be proscribed by its injurious effect on the cultivated crop even though it may otherwise provide excellent control of weeds plaguing that crop.

To preserve the beneficial aspects of herbicide use and to mitigate crop damage, many herbicidal antidotes have been prepared. These antidotes reduce or eliminate damage to the crop without substantially impairing the beneficial effect of the herbicide. For example, see U.S. Pat. Nos. 4,021,224 and 4,021,229 and Belgian Patent No. 846,894.

Although several explanatory theories have been advanced, the precise mechanism by which an antidote reduces herbicidal injury to crops while providing weed control has not been conclusively verified. An antidote compound may in fact be a remedy, interferent, protectant, or antagonist. As used herein, "antidotal" compound or "antidote" describes the effect which preserves herbicidal phytotoxicity to weed species while reducing crop injury, i.e., establishes herbicidal selectivity, vis-a-vis the herbicide.

As an alternative mode of action, the compounds of this invention may interfere with the normal herbicidal action of the thiocarbamate-type herbicides to render them selective in their action. Whichever mode of action is present, the corresponding beneficial and desirable effect is the continued herbicidal effect of the thiocarbamate with the accompanying decreased herbicidal effect on desired crop species. This advantage and utility will become more apparent hereinafter.

Therefore, the terms herbicide antidotes or antidotal amount, is meant to describe that effect or the amount which produces the effect which tends to counteract the normal injurious herbicidal response that the herbicide might otherwise produce. Whether it is to be termed a remedy, interferent, protectant, or the like, will depend upon the exact mode of action. The mode of action is varied, but the effect, which is desirable, is the result of the method of treating the soil in which a crop is planted.

Prior Art

Thiolcarbamate herbicides are particularly effective in the control of grassy type weeds which interfere with the cultivation of a wide variety of crops, e.g., barley, corn, lentils, peanuts, peas, potatoes, soybeans, spinach, tobacco and tomatoes.

Trifluralin is used for weed control primarily in cotton, soybeans, and sugarbeets. Frequently, their beneficial use of these herbicides can be enhanced by the addition of an antidotal compound.

DESCRIPTION OF THE INVENTION

It has been discovered that certain sulfinoate compounds are novel compounds and are particularly effective as antidotes for the protection of corn from thiolcarbamate herbicidal injury and of wheat and rice from trifluralin herbicidal injury. Sulfinoate compounds have the formula:

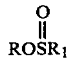

in which R and $R_1$ are each haloalkyl having 1-4 carbon atoms. In its preferred embodiment, R is $\beta$-chloroethyl and $R_1$ is dichloromethyl. As new compounds, it is provided that $R_1$ is other than trifluoromethyl.

The present invention includes a herbicidal composition comprised of:

(a) a herbicidally effective amount of a thiolcarbamate of the formula:

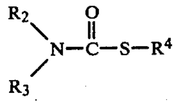

in which $R_2$ is selected from the group consisting of alkyl having 1-6 carbon atoms and alkenyl having 2-6 carbon atoms;

$R_3$ is selected from the group consisting of alkyl having 1-6 carbon atoms, alkenyl having 2-6 carbon atoms, cyclohexyl and phenyl; or $R_2$ and $R_3$ taken together with the nitrogen form a heterocyclic ring having 5-10 carbon atoms; and $R_4$ is selected from the group consisting of alkyl having 1-6 carbon atoms, haloalkyl having 1-4 carbon atoms, cycloalkyl having 5-10 carbon atoms, phenyl, substituted phenyl, wherein the substituents are alkyl having 1-4 carbon atoms, haloalkyl having 1-4 carbon atoms, and halo, benzyl, and substituted benzyl, wherein the substituents are alkyl having 1-4 carbon atoms, haloalkyl having 1-4 carbon atoms, and halo;

(b) a non-phytotoxic antidotally effective amount of a sulfinoate of the formula:

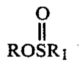

in which R and $R_1$ are each haloalkyl having 1-4 carbon atoms.

By way of exemplification, the active thiolcarbamate herbicides employed in the invention may include the following: EPTC, S-ethyl diisobutyl thiocarbamate, S-propyl dipropyl thiocarbamate, S-2,3,3,-trichloroallyldiisopropyl thiocarbamate, S-ethyl cyclohexyl ethyl thiocarbamate, S-ethyl hexahydro-1H-azepine-1-carbothioate, S-4-chlorobenzyl diethyl thiocarbamate, and combinations thereof.

This invention also includes a herbicidal composition comprised of:

(a) a herbicidally effective amount of a trifluralin of the formula:

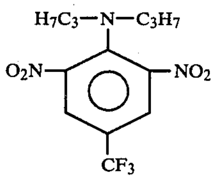

and (b) a non-phytotoxic antidotally effective amount of a sulfinoate of the formula:

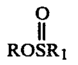

in which R and $R_1$ are each haloalkyl having 1-4 carbon atoms.

The terms "alkyl" and "alkenyl" as used herein are intended to include both straight- and branched-chain groups. All carbon atom ranges are intended to be inclusive of both upper and lower limits. The term "halo" is used to include mono and poly halo groups including chloro, bromo and fluoro and mixtures thereof. Exemplary of "alkyl" are methyl, ethyl, n-propyl, isopropyl, n-butyl, isobutyl, tertiarybutyl, pentyl, hexyl, and the like. Exemplary of "alkenyl" are such groups as vinyl, proenyl, butenyl, pentyl, hexenyl, and the like. Exemplary of cycloalkyl are cyclopentyl, cyclohexyl, 2,2 dimethyl cyclohexyl, cycloheptyl, and the like.

This invention also includes the method of protecting crops from thiocarbamate or trifluralin herbicidal injury which comprises applying to the locus where protection is desired a non-phytotoxic antidotally effective amount of a sulfinoate compound of the formula:

in which R and $R_1$ are each haloalkyl having 1-4 carbon atoms.

PREPARATION

The thiocarbamates of the present compositions can be prepared by the procedures described in U.S. Pat. Nos. 2,913,327, 3,185,720, 2,983,747, 3,133,947 and 3,198,786.

The sulfinoates of the present invention were synthesized by the following two-step process.

I. The reactant benzyl dichloromethyl sulfoxide was prepared by dissolving 15.4 grams (g) of benzyl dichloromethyl sulfide in 100 milliliters (ml) of methylene chloride. The solution was cooled in an ice-bath and 15 g of 85% 3-chloroperbenzoic acid was added. After stirring overnight at room temperature, the solution was washed with a 5% solution of potassium carbonate. It was then dried and the solvent evaporated, yielding 15.5 g of solid white benzyl dichloromethyl sulfoxide (m.p. 84°-90° C.). Structure was confirmed by infrared spectraphotometric analysis (IR), and nuclear magnetic resonance spectrum (NMR).

II. Four grams of N-chlorosuccinimide were slurried into 150 ml of carbon tetrachloride. While the solution was cooled in an ice-bath, there was added 6.1 g of the freshly prepared benzyl dichloromethyl sulfoxide and a second solution of 2.2 g of chloroethanol dissolved in 40 ml methylene chloride. The reaction mixture was stirred overnight at room temperature.

Following filtration and water washing of the solution, the solvent was removed. The residue was distilled at 0.1 mm at a boiling point between 80°-100° C., yielding 2.7 g of β-chloroethyl-dichloromethyl sulfinoate. Structure was confirmed by IR and NMR.

TESTING

The thiocarbamate herbicides used to test the present invention can be prepared by the procedures described in expired U.S. Pat. No. 2,913,327. Trifluralin can be prepared by the procedure described in U.S. Pat. No. 3,257,190.

Stock solutions of the thiocarbamates were prepared by dissolving the requisite amount of the herbicide in water. A standarized solution of trifluralin was prepared in the same manner. The solution compositions and their equivalent rates of application appear in Table I.

TABLE I

| Herbicidal Solutions | | | |
|---|---|---|---|
| Solution Composition | | Application Rate | |
| Herbicide (mg) | Water (ml) | ml/flat | ~lb/acre |
| S-propyldipropyl-thiocarbamate | | | |
| 550 | 400 | 4.0 | 1.00 |
| 2730 | 400 | 4.0 | 5.00 |
| S-ethyl N,N-dipropyl thiocarbamate | | | |
| 2666 | 500 | 5.0 | 5.00 |
| trifluralin | | | |
| 1798 | 800 | 4.0 | 1.00 |
| 1350 | 400 | 4.0 | 1.50 |

The antidote stock solution was prepared by dissolving requisite amounts of β-chloroethyl-dichloromethyl sulfinoate in acetone. The solution compositions and their equivalent rates and methods of application appear in Table II.

TABLE III

| Antidote Stock Solutions Antidote: β-chloroethyl-dichloromethylsulfinoate | | | | |
|---|---|---|---|---|
| Composition | | Application | | |
| Antidote (mg) | Acetone (ml) | ml/flat ~ lb/acre | | Method* |
| 95 | 15 | 0.30 | 1.00 | IF |
| 95 | 15 | 1.50 | 5.00 | IF |
| 10 | 100 | 2.00 | 0.05 | PPI |

*IF = In-furrow surface application.

PPI = Pre-plant incorporation of herbicide and antidote as a tank mix.

All of the soil used in the tests described herein was loamy sand soil treated with 50 parts per million (ppm) each of a commercially available fungicide, cis-N[(trichloromethyl)thio]-4-cyclohexene-1,2-dicarboximide, and an 18-18-18 fertilizer, which contains 18% by weight equivalent each of nitrogen, phosphorus pentoxide, and potassium oxide.

The herbicides were applied to the soil by pre-plant incorporation (PPI) of the herbicide into the soil as a tank mix using a five gallon rotary mixer. The antidote β-chloroethyl-dichloromethyl sulfinoate was combined in this manner when tested with S-ethyl N,N-dipropyl thiocarbamate.

The antidote was applied by the in-furrow (IF) method when tested with either S-propyl dipropyl thiocarbamate or trifluralin which were previously incorporated into the soil by PPI.

For the IF antidote applications, a one pint (473 cubic centimeter) sample of soil from each planting flat was removed and retained. After leveling and furrowing the soil, seeds of the crop or weed species were planted ½ inch (1.27 centimeter) deep. Each flat was divided in half by a wooden barrier. A stock solution of the antidote was atomized directly onto the exposed seeds and soil in the open furrow on one side of the barrier. The seeds in the entire flat were then covered with the previously removed soil. The antidotally untreated sections of flats were compared for observed differences which would indicate lateral movement of the antidote through the soil.

Soil filled flats were planted with seeds of a single crop or weed species.

The treated crops screened for diminution of herbicidal injury were milo, wheat, cotton, rice, barley, corn, and soybeans. The weed species tested for control was foxtail (*Setaria viridis*).

All flats were placed on greenhouse benches where temperature was maintained between 70° and 90° F. (21.1° to 32.2° C.). The flats were watered by sprinkling as needed to assure good plant growth.

Control flats contained crops treated with herbicides only at the various rates and methods of application.

Injury ratings were taken four weeks after application of the antidotes. The effectiveness of the antidote was determined by visual comparison of injuries to crops and weeds in the control and test flats to those in untreated flats. The results appear in Table III.

TABLE III

Herbicidal and Antidotal Effectiveness

| β-Chloroethyl-dichloromethyl-sulfinoate | | Herbicide | | % Injury | | | | | | | | | | | | | | | |
|---|---|---|---|---|---|---|---|---|---|---|---|---|---|---|---|---|---|---|---|
| | | | | Milo | | Wheat | | Cotton | | Rice | | Barley | | Corn | | Soybean | | Foxtail | |
| Rate[1] | Method | Name | Rate | U | T | U | T | U | T | U | T | U | T | U | T | U | T | U | T |
| 5.00 | IF | VERNAM ®[2] | 1.00 | 100 | — | 78 | — | | | 65 | — | 35 | — | | | | | | |
| 5.00 | IF | VERNAM | 5.00 | | | | | 85 | — | | | | | 75 | 0 | 40 | — | | |
| 0.05 | PPI | EPTAM ®[3] | 5.00 | | | | | | | | | | | 80 | — | | | 100 | — |
| 5.00 | IF | TRIFLURALIN | 1.00 | 100 | — | 100 | 20 | | | 95 | 30 | | | | | | | 100 | — |
| 1.00 | IF | TRIFLURALIN | 1.50 | | | | | | | 90 | 70 | | | | | | | | |
| 5.00 | IF | TRIFLURALIN | 1.50 | | | | | | | 95 | 70 | | | | | | | | |
| 1.00 | IF | TRIFLURALIN | 1.50 | | | 80 | 65 | | | | | | | | | | | | |
| 5.00 | IF | TRIFLURALIN | 1.50 | | | 80 | 50 | | | | | | | | | | | | |

[1]All rates are in pounds per acre.
[2]VERNAM ® = S-propyl N,N-dipropylthiocarbamate
[3]EPTAM ® = S-ethyl N,N-dipropylthiocarbamate
Injury Ratings:
U = Antidotally untreated; % Injury 4 weeks after herbicide application.
T = Antidotally treated; % Injury 4 weeks after treatment with herbicide plus antidote compound.
— = Indicates no change.

FORMULATIONS

The compositions can be formulated in the same manner in which herbicides are generally formulated. The object of the formulation is to apply the compositions to the locus where control is desired by a conventional method. The "locus" may include soil, seeds, seedlings, and vegetation.

The active herbicidal ingredient of a formulation will generally be such that its application rate will be within the range of 0.1 to 50 lb/A (0.112 to 56 k/ha). The antidote compound which may be formulated separately or together with the herbicide will generally comprise about 0.01 to about 30 parts by weight of the herbicide.

Formulations will generally contain several additives. Among these are some inert ingredients and diluent carriers such as organic solvents, water, oil and water, water in oil emulsions, carriers of dusts and granules, and surface active wetting, dispersing, and emulsifying agents. Fertilizers, e.g., ammonium nitrate, urea and superphosphate, may also be included. Aids to rooting and growth, e.g., compost, manure, humus, sand, etc., may likewise be included. The formulations are commonly dusts, wettable powders, granules, solutions or emulsifiable concentrates.

Dusts are free-flowing powder compositions containing the herbicidal compound impregnated on a particulate carrier. The particle size of the carriers is usually in the approximate range of 30 to 50 microns. Examples of suitable carriers are talc, bentonite, diatomaceous earth, and pyrophyllite. Anti-caking and anti-static agents can be added, if desired. The composition generally contains up to 50% of active ingredient. Dusts, like liquid compositions, can be applied by spraying from boom and hand sprayers or airplanes.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in Wade Van Valkenburg, *Pesticide Formulations* (Marcel Dekker, Inc., N.Y., 1973) at pages 79–84.

Granules comprise the herbicidal composition impregnated on a particulate inert carrier having a particle size of about 1 to 2 millimeters in diameter. The granules can be made by spraying a solution of the active ingredient in a volatile solvent onto the granular carrier. Suitable carriers in preparation of granules include clay, vermiculite, sawdust, granular carbon, etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The compounds and compositions of this invention can also be applied by addition to irrigation water supplied to the field to be treated. This method of application permits the penetration of the compositions into the soil as the water is absorbed therein.

It is not necessary that the compounds and compositions be admixed with the soil particles. After application by the above discussed methods, they may be distributed below the surface to a depth of at least one-half inch by conventional means such as discing, dragging, or mixing.

I claim:

1. A herbicidal composition consisting essentially of (a) a herbicidally effective amount of trifluralin; and (b) a non-phytotoxic antidotally effective amount of a sulfinoate of the formula:

in which R and $R_1$ are each haloalkyl having 1–4 carbon atoms.

2. A herbicidal composition according to claim 1 consisting essentially of:

(a) a herbicidally effective amount of trifluralin; and (b) a non-phytotoxic antidotally effective amount of β-chloroethyl-dichloromethylsulfinoate.

3. A method of controlling undesirable vegetation while reducing herbicidal injury to wheat and rice crops due to trifluralin which comprises applying to the locus where control is desired a non-phytotoxic antidotally effective amount of a compound of the formula:

in which R and $R_1$ are each haloalkyl having 1–4 carbon atoms.

4. The method of claim 3 in which the locus is soil in which a herbicidally effective amount of said trifluralin has been added.

5. The method of claim 4 in which R is β-chloroethyl and $R_1$ is dichloromethyl.

* * * * *